United States Patent
Kong et al.

(10) Patent No.: US 9,090,913 B2
(45) Date of Patent: Jul. 28, 2015

(54) SEQUENCE OF PORCINE ROSA26 LOCUS AND METHODS OF USING THE SAME

(71) Applicants: Qingran Kong, Harbin (CN); Meiling Wu, Harbin (CN); Zhonghua Liu, Harbin (CN)

(72) Inventors: Qingran Kong, Harbin (CN); Meiling Wu, Harbin (CN); Zhonghua Liu, Harbin (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 13/887,316

(22) Filed: May 4, 2013

(65) Prior Publication Data

US 2014/0331345 A1    Nov. 6, 2014

(30) Foreign Application Priority Data

May 4, 2012    (CN) .......................... 2012 1 0134764

(51) Int. Cl.
*C12N 15/00* (2006.01)
*C07H 21/04* (2006.01)
*C12N 15/90* (2006.01)
*C12N 15/79* (2006.01)
*C12N 15/85* (2006.01)

(52) U.S. Cl.
CPC .............. *C12N 15/907* (2013.01); *C12N 15/79* (2013.01); *C07H 21/04* (2013.01); *C12N 15/85* (2013.01)

(58) Field of Classification Search
CPC ...... C12N 15/79; C12N 15/85; C12N 15/907; C07H 21/04
USPC ...................................... 435/320.1; 536/23.1
See application file for complete search history.

(56) References Cited

PUBLICATIONS

McLaren, S., 2009, GenEmbl Accession No. CU929960, computer printout pp. 4-12.*
Humphray et al., 2005, EST Accession No. CT300665, computer printout pp. 6-7.*
Kuhn et al., 2013, US 20130212725 A1, effective filing date Jun. 7, 2010.*

* cited by examiner

*Primary Examiner* — Shin Lin Chen
(74) *Attorney, Agent, or Firm* — Lili Chen

(57) ABSTRACT

The present invention provides a 5 kb sequence of porcine ROSA26 locus, which can be used for site-specific integration of an exogenous gene into a pig genome. The present invention also provides a gene targeting vector with a 3' and 5' arm of the porcine ROSA26 sequence, wherein a target gene can be inserted between the 3' and 5' arm sequence. The gene targeting vector can be used to generate transgenic pigs with stable and ubiquitous expression of the target gene.

3 Claims, 7 Drawing Sheets

SEQUENCE OF PORCINE ROSA26 LOCUS AND METHODS OF USING THE SAME

CROSS-REFERENCES AND RELATED APPLICATIONS

This application claims priority of Chinese Application No. 201210134764.0, entitled "The sequence of porcine ROSA26 locus and methods of using the same", filed May 4, 2012, which is herein incorporated by reference in its entirety.

BACKGROUND OF THE INVENTION

1. Field of the Invention

The present invention relates to the field of genetic engineering, and more particularly relates to methods of targeting endogenous and exogenous genes to transgenic animals through homologous recombination.

2. Description of the Related Art

Over the past decade, transgenic technology has developed rapidly and been widely applied to different areas. Combined with cloning technology, it makes possible for bringing transgenic animals from basic research to industrial production. Expressing target genes stably and efficiently in transgenic animals has been a great challenge for its application in industrial production. One important factor affecting the expression efficiency of a target gene is integration sites of target genes in host genomes. Therefore, identification and characterization of sequences associated with high efficiency integration and stable expression of target genes is very important for industrial application of transgenic animals.

The ROSA26 was originally identified as a ubiquitous marker in a retroviral gene-trapping screen in mouse embryonic stem cells. The promoter for ROSA26 gene was found to drive widespread expression of transgenes, and the promoter region and the first intron of the ROSA26 forward transcript has been established as the preferred integration site for the high targeting efficiency and the ubiquitous expression of reporter genes in transgenic mice. There are many transgenic mice reported, such as Zambrowicz et al (Disruption of overlapping transcripts in the ROSA beta geo 26 gene trap strain leads to widespread expression of beta-galactosidase in mouse embryos and hematopoietic cells. Proc Natl Acad Sci USA, 1997, 94(8): 3789-3794), Kisseberth et al (Ubiquitous expression of marker transgenes in mice and rats. Dev Biol, 1999, 214(1): 128-138). In 2007, Trion et al. have documented the identification and characterization of a human homolog of the mouse Rosa26 locus in human embryonic stem cells and demonstrated that transgenes can be readily introduced and broadly expressed in the different lineages of human cells via homologous recombination at the human Rosa26 locus (Trion et al. Identification and targeting of the ROSA26 locus in human embryonic stem cells. Nat Biotechnol, 2005, 25: 1477-1482). Although, the ROSA26 gene has been used widely in transgenic mice, there is no application of ROSA26 gene in transgenic livestock.

The previous studies of transgenic livestock largely rely on random integration of target genes into the livestock genome. This can be problematic as transgenes introduced into random sites with multiple copies are often subjected to position effect variegation (PEV) and repeat-induced gene silencing (RIGS). The method causes the high variability of expression which frequently happens by random integration due to transgenes inserted at random and at various copy numbers into the host genome. In addition, multiple transgene copies and unpredicted integration sites also makes it difficult for identification of transgenic animals, which has been an obstacle for widespread usage of transgenic animals in industrial production. Research shows that targeted transgensis though homologous recombination can provide a solution to the problems above. However, targeted transgensis has only been applied successfully in transgenic mice, fewer in other transgenic livestock, especially no application in transgenic pigs.

There is a need for identifying genomic locus with high homologous combination frequency and ubiquitous transcriptional activity in pigs. The present invention satisfies this need and provides other benefits as well.

DETAILED DESCRIPTION

The present invention provides a method for site-specific integration of target genes at porcine Rosa26 locus, which solves the problem of unstable and inefficient expression of target genes in transgenic pigs. Using the sequence of mouse Rosa locus as a template to search the pig genome sequence database, a sequence homologous to moue Rosa26 locus is identified in the pig genome. The identified porcine Rosa26 locus, mapped to pig chromosome 13, includes a promoter, a first exon, a first intron, and a second exon.

In one embodiment, the present invention provides an isolated nucleotide sequence of porcine ROSA26 gene for site-specific gene targeting, comprising one sequence selected from the group consisting of:
1) a nucleotide sequence set forth in SEQ ID NO:1 (porcine Rosa26 locus);
2) a nucleotide sequence that can hybrid to the DNA sequence of SEQ ID NO: 1 under stringent hybridization conditions; and
3) a nucleotide sequence having at least 95% sequence identity with SEQ ID NO: 1.

In another embodiment, the present invention provides a gene targeting vector for site-specific integration and stable expression of a target gene in a transgenic animal, wherein the gene targeting vector comprises a 5' arm and a 3' arm of the porcine Rosa26 locus and the target gene is inserted between the 5' arm and 3' arm of the porcine Rosa26 locus. The 3' arm and 5' arm can be, for example, 3.6 kb and 1.4 kb in length, respectively. In a preferred embodiment, the present invention provides a gene targeting plasmid with a DNA sequence set forth in SEQ ID NO:2.

In another embodiment, The present invention provides a method for site-specific integration and stable expression of a target gene in transgenic animals, comprising the steps of:
1) construct a gene targeting vector, wherein the gene targeting vector comprises the target gene inserted between a 5' arm and 3' arm of the porcine Rosa26 locus;
2) use the gene targeting vector to make a transgenic animal, wherein the target gene is site-specifically integrated and stably expressed in the transgenic animal.

In a preferred embodiment, the transgenic animals are transgenic pigs and the gene targeting vector comprises the DNA sequence of SEQ ID NO:2.

The present invention provides a 5 kb sequence of porcine ROSA26 locus that can be effectively used for site-specific integration and stable expression of target genes in pigs. The present invention provides a method of using the porcine ROSA26 sequence to insert a target gene into a transgenic pig, which can protect the target gene from immune-mediated rejection and epigenetic modification, enabling the target gene to be expressed stably and efficiently in large livestock animals like pigs.

A: Gene map of plasmid pPNT6, B: a schematic representation of

Figure 4:
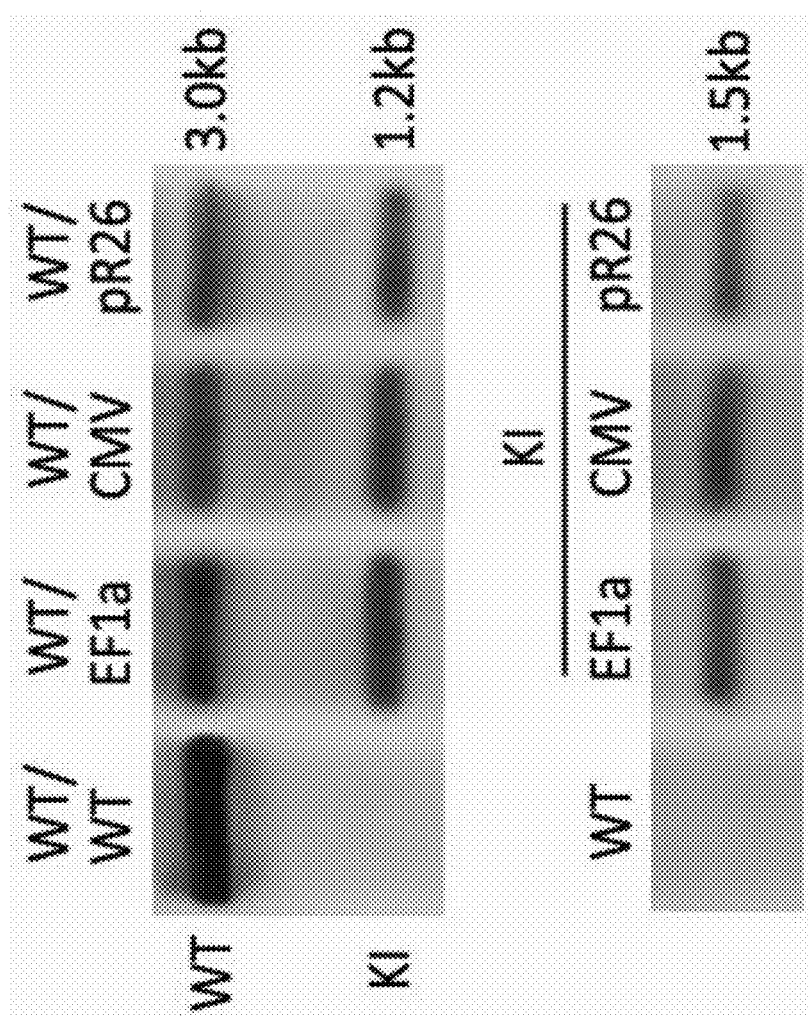

FIG. 4. Southern blot analysis of GFP expression at the porcine ROSA26 locus

Figure 5:
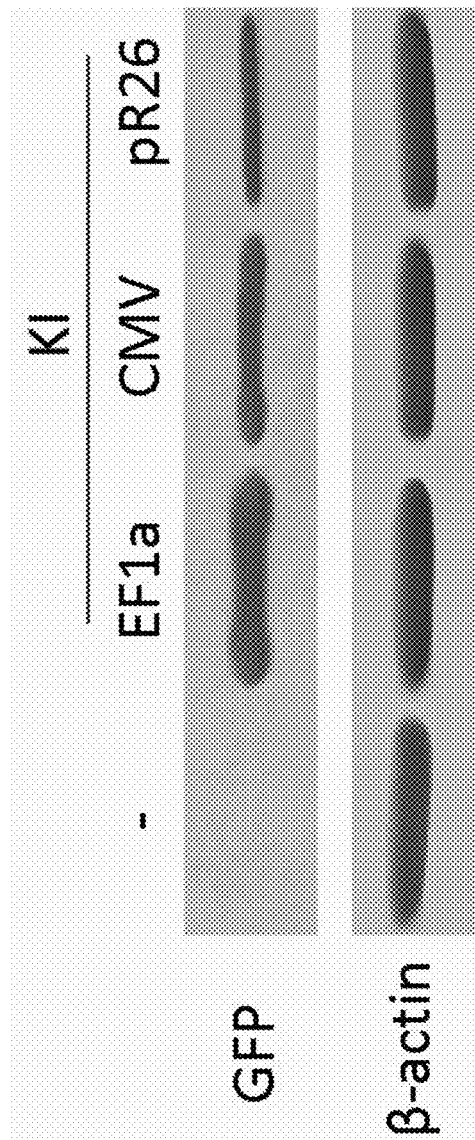

FIG. 5. Western blot analysis of GFP expression in targeted cell lines

Figure 6:
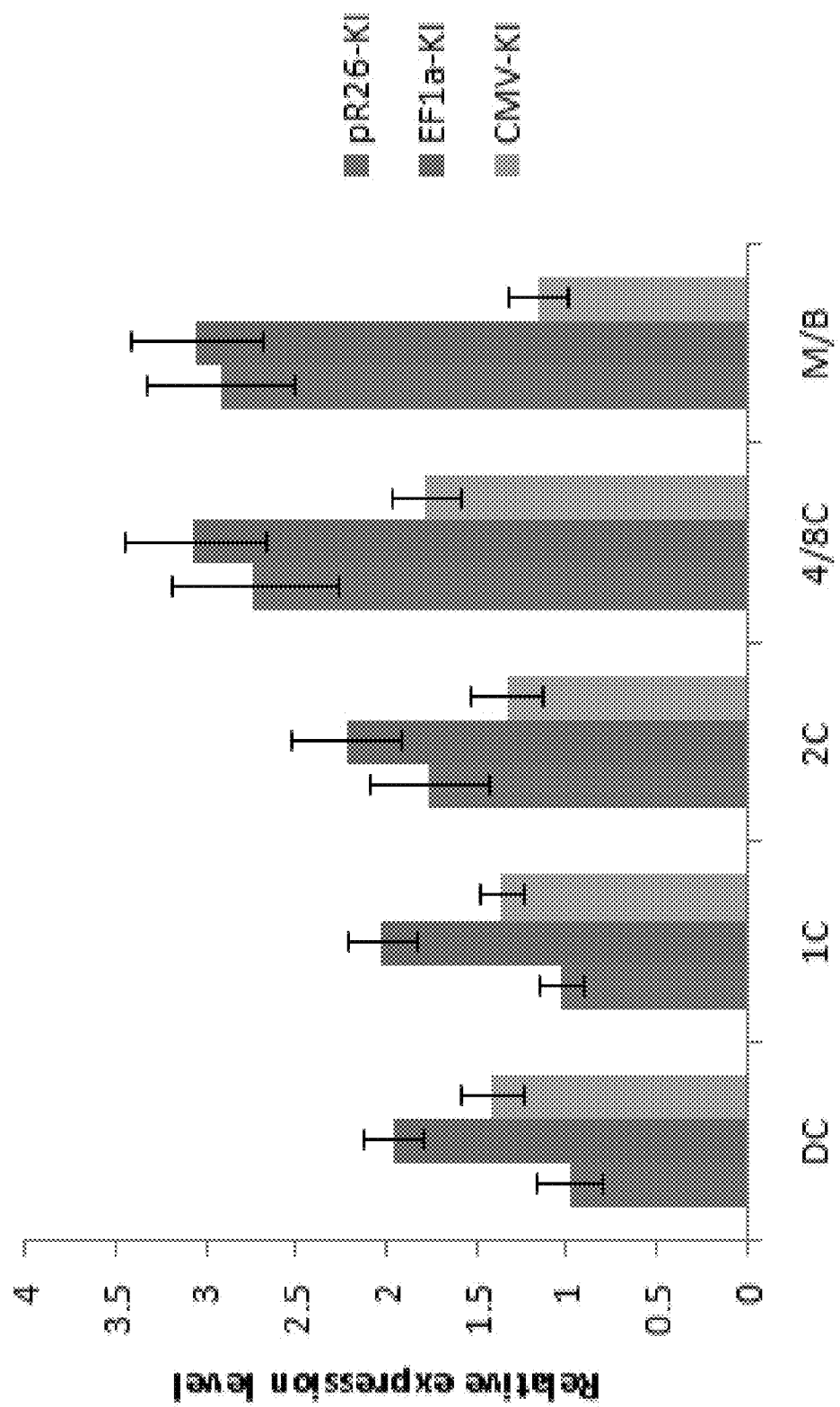

FIG. 6. Targeted GFP expression in cells at different developmental stages. DC, donor cells; 1C, 1-cell stage embryos; 2C, 2-cell stage embryos; 4/8C, 4 and 8-cell stage embryos; M/B, morula and blastocyst.

Figure 7:
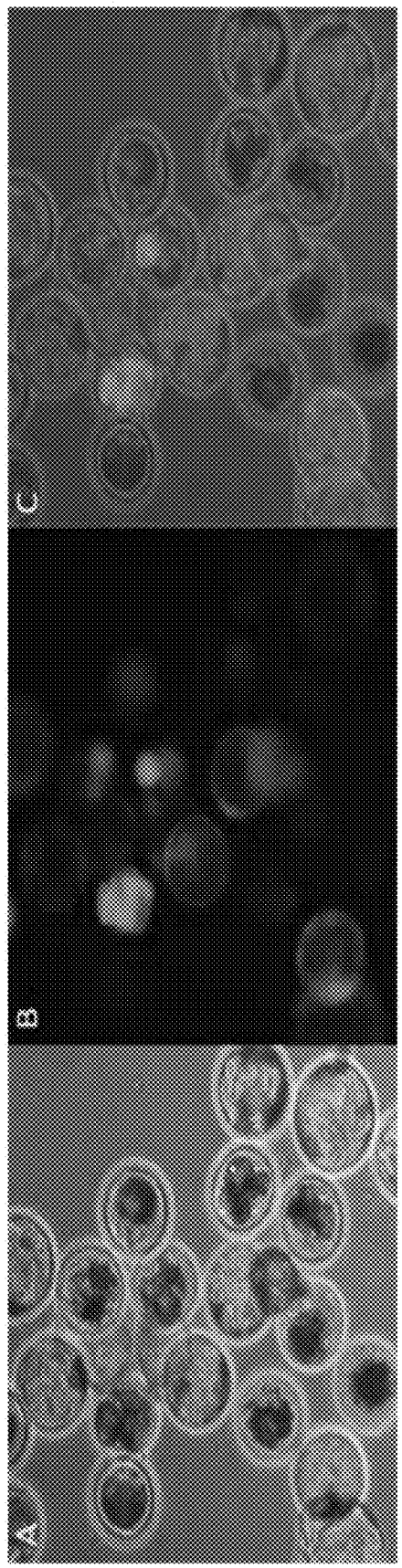

FIG. 7. GFP expression in transgenic blastocysts

A: under normal light, B: under FITC light, C: merged images.

EXAMPLES

The present invention can be better understood and illustrated by the following examples. The following examples were provided by way of illustration only, and not by way of limitation.

Example 1

The Sequence of Porcine ROSA26 Locus

The sequence of porcine ROSA26 locus is set forth in SEQ ID NO: 1. The porcine ROSA26 sequence can be used in a gene targeting vector (as described below) to specifically target a single copy of exogenous gene to a homologous ROSA26 locus in pig genome and drive stable and ubiquitous expression of the exogenous gene. DNA sequences that can hybridize with porcine ROSA16 gene under stringent hybridization conditions (e.g. hybridization temperature: $T_m$-10° C. to $T_m$-15° C.), which can be used to promote expression of target genes, are also included in the scope of the presently claimed invention. Also included are DNA sequences with high sequence identity (>=90%) with the porcine ROSA25 sequence of SEQ ID NO:1.

Example 2

Identification of the Porcine ROSA26 Sequence

The ROSA26 gene was mapped to chromosome 13 in pig genome by a BLAST search of genomic sequences homologous to mouse ROSA26 sequence (Zambrowicz B. et al. Disruption of overlapping transcripts in the ROSA beta geo 26 gene trap strain leads to widespread expression of beta-galactosidase in mouse embryos and hematopoietic cells. Proc Natl Acad Sci USA. 1997, 94(8):3789-94.). Most sequence information was released in NCBI Sscrofa10.2 database. However, there was a gap, about 108 bp, in 3-terminal of porcine ROSA26 gene first intron. Based on sequences flanking the gap, the primers for PCR amplification were designed as: 5'-GGATCTAATTGGAGC-TATAACTGCCAGC-3' (forward) (SEQ ID NO: 3) and 5'-GCTGAGGGTCCCAAATGCTTTG-3' (reverse) (SEQ ID NO: 4). The PCR amplification was performed as described: 3 min incubation at 94° C. to denature the DNA templates, 30 cycles of 30 seconds at 94° C., 30 seconds at 60° C., 1 minute at 72° C., then 10 minutes at 72° C., end with one hour at 4° C. A sequence, including a promoter, a first exon, a first intron and a second exon of the porcine ROSA26 gene, was isolated by PCR amplification. The identified porcine ROSA26 sequence could be used to protect target genes expression in transgensis.

Example 3

Construction of a Gene Targeting Plasmid Based on the Porcine ROSA26 Sequence

Figure 1:
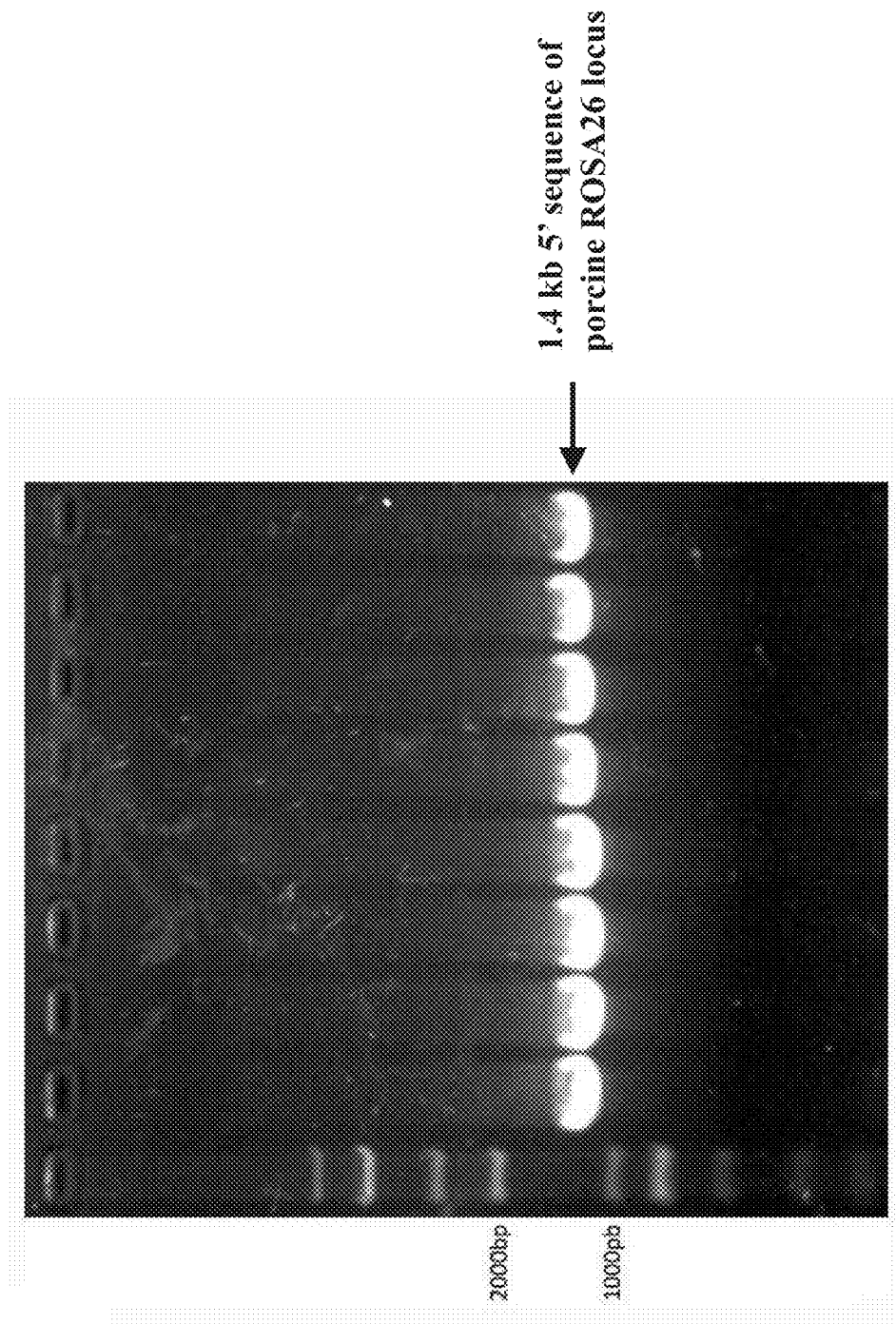
FIG. 1. Isolation and identification of 5'-terminal porcine ROSA26 sequence by PCR amplification (1.4 kb)
Figure 2:
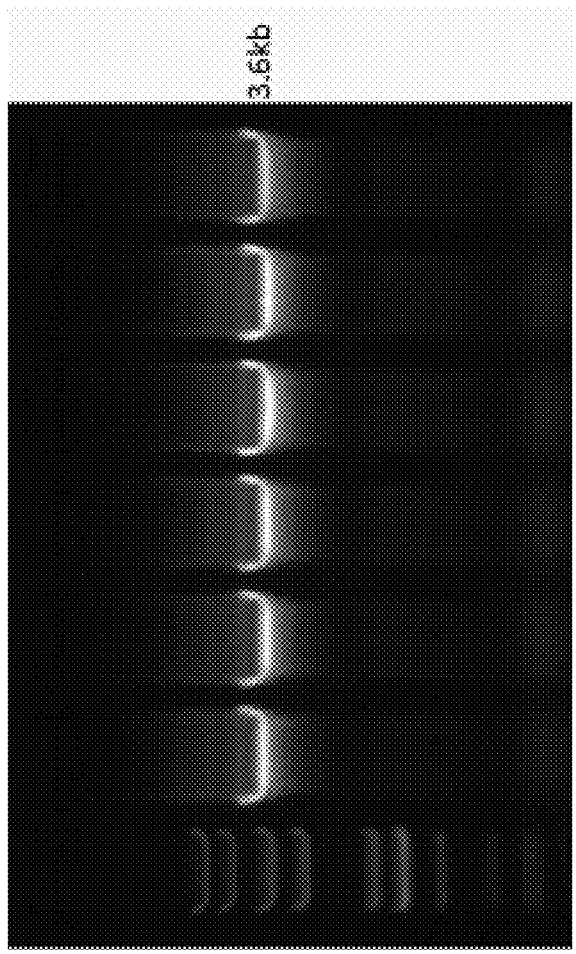
FIG. 2. Isolation and identification of 3'-terminal porcine ROSA26 sequence by PCR amplification (3.6 kb)
Figure 3:
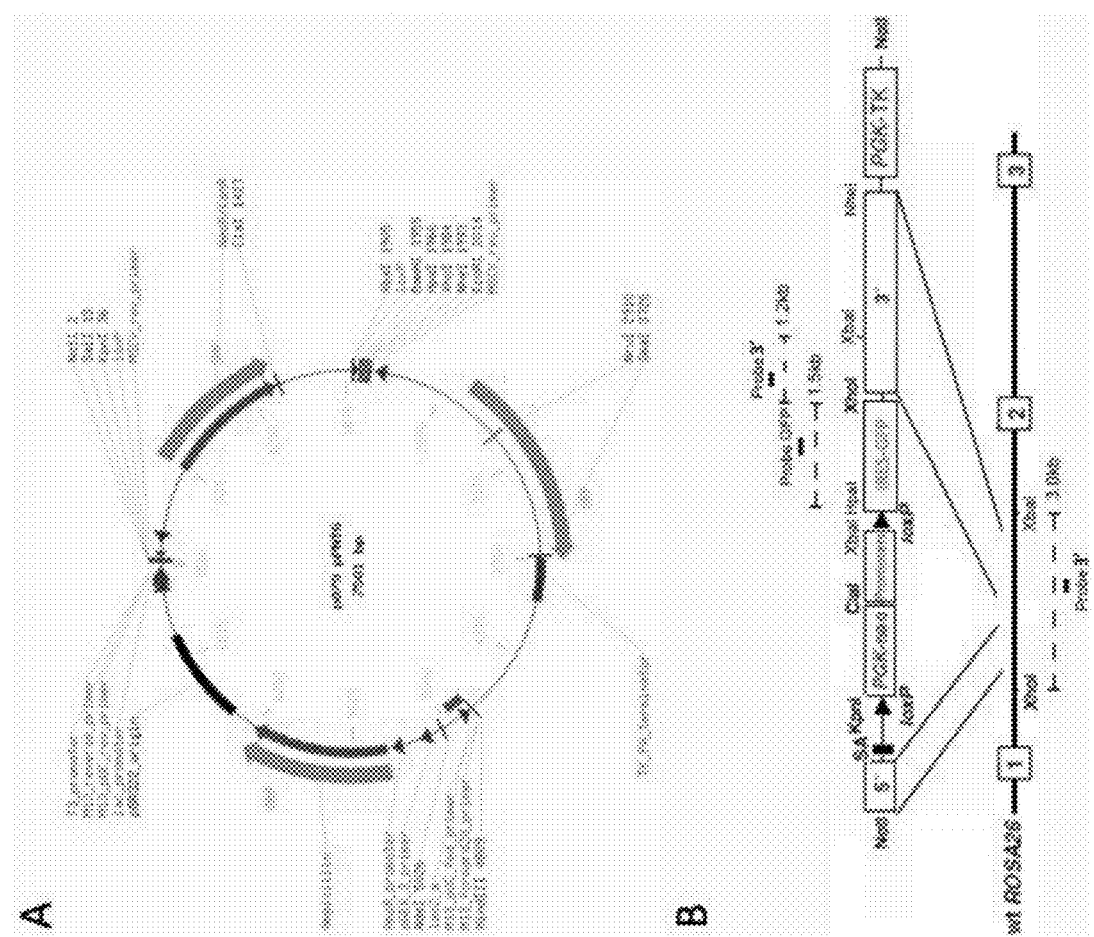
FIG. 3. Gene targeting Plasmid construction

A gene targeting plasmid based on the porcine ROSA26 sequence was constructed as shown in FIG. 3. The sequence of the gene targeting plasmid was set forth as SEQ ID NO: 2. To construct a gene targeting plasmid, a 1.4 kb 5'-terminal short arm and a 3.6 kb 3'-terminal long arm were amplified, sequenced and subcloned into PPNT6 plasmid at 5' NotI/3' KpnI and 5' XhoI/3' NheI restriction sites, respectively. The primer sequences for amplifying 5'-terminal arm and 3'-terminal arm were listed as follows:

5'-CGGGAGTGCGGCCCGCCCTGCGGC-3' (5-terminal arm, forward) (SEQ ID NO:5)
5'-AGTAGATCCGTGCTTTTTAACCTATC-3' (5-terminal arm, reverse) (SEQ ID NO: 6)
5'-GAGTTTTACAGTCATCCCATTTGTAGACTTTTGC-3' (3-terminal arm, forward) (SEQ ID NO: 7)
5'-AGCTCTGATCCCGTGT TGTTGTGGCATAG-3' (3-terminal arm, reverse) (SEQ ID NO:8)

Also, the sequence of IRES-GFP from TRE plasmid (Addgene) was subcloned into PPNT6 plasmid at 5'HpaI/3' XhoI restriction site. The pR26, CMV and EF1a promoters are inserted at 5' ClaI/3' XbaI restriction site to construct targeting vector PPNT6/pR26, PPNT6/CMV and PPNT6/EF1a, respectively.

Example 4

Analysis of Target Gene Expression Via Site-Specific Integration at Porcine ROSA26 Locus Genomic sequences from gene targeting transgenic cells were digested with XhoI/XbaI and used for southern blot analysis. The hybridization probe used to detect the GFP transcription unit DNA (probe GFP) was synthesized by PCR, which yields a 757 bp product, and the sequences of the primers were 5'-GAGCAAGGGCGAGGAGCTGTTCA-3' (forward) (SEQ ID NO: 9) and 5'-TGCAGAATT CGAAGCTTGAGC-3' (reverse) (SEQ ID NO:10). Another probe identifying the 3-terminal arm of ROSA26 locus (probe 3') was synthesized by PCR, which yields a 360 bp product, and the sequences of the primers were 5'-GTTAGTAACT-GAGCTCAGTTGCCG-3' (forward) (SEQ ID NO: 11) and 5'-GGGAACCA CCCTACAGAGATCTG-3' (reverse) (SEQ ID NO: 12).The PCR products were labeled by DIG Oligonucleotide 3'-End Labeling Kit (Roche). This 3' probe can recognize a 3 kb genomic sequence in the pig genome when digested with XhoI/XbaI. In the gene targeting plasmid, this 3' probe recognizes a shorter sequence of 1.2 kb when cut by the same enzymes (see FIG. 3b). By Southern blot analysis, the probe 3' detected an identical band (about 3.0 kb) in both transgenic cells and wild cells (WT). There was another band (about 1.2 kb) present in transgenic cells, which confirmed the fact that the target gene was a single copy integration in genome. In addition, there was also a single band (about 1.5 kb) detected using probe GFP in transgenic cells, which indicated that the GFP was integrated into the genome.

Southern Blot

1. Probe Synthesis, Purification and Labeling (1) Probe preparation, the vector pEGFP-C1 (Clontech) was used as a template for PCR amplification of a GFP probe. The primers were designed as: 5'-GAGCAAGGGCGAG GAGCTGTTCA-3' (forward) (SEQ ID NO: 9) and 5'-TGCA-GAATTCGAAGCTTGAGC-3' (reverse) (SEQ ID NO: 10). The PCR amplification was performed as follows: 3 minutes at 94° C.; 30 cycles of 30 s at 94° C., 30 s at 65° C. minus, 1 minute s at 72° C.; 10 minutes at 72° C. for final extension, and, end with one hour at 4° C. The PCR product (about 752 bp) was isolated for purification of GFP probe.

(2) Probe purification, the GFP probe was purified using TIANquick Midi Purification Kit (Beijing Tiangen, LTD.) The purification was performed as follows:
1) Column equilibration: add 500 ul Buffer BL to the Spin Column CB2. Centrifuge for 1 min at 12,000 rpm (~13400×g) in a table-top microcentrifuge. Discard the flow-throw, and then place Spin Column CB2 in the collection tube.
2) Add 5 volumes of Buffer PB to 1 volume of the PCR reaction, and mix them.
3) Transfer the mixture to the Spin Column CB2 (Placing Spin Column CB2 back into the same collection tube). Let it stand for 2 min at room temperature. Centrifuge for 30-60 s at 12,000 rpm (~13400×g) in a table-top microcentrifuge. Discard the flow-throw, and then place Spin Column CB2 back into the same collection tube.
4) Add 700 µl Buffer PW to the Spin Column CB2 and centrifuge for 30-60 s at 12,000 rpm (~13,400×g). Discard the flow-through, and place Spin Column CB2 back in the same collection tube.
5) Wash the Spin Column CB2 with 500 µl Buffer PW and centrifuge for 30-60 s at 12,000 rpm (~13,400×g). Discard the flow-through, and centrifuge for an additional 2 min to remove residual wash buffer PW.
6) Place the Spin Column CB2 in the same collection tube, and centrifuge for 2 min at 12,000 rpm (~13,400×g) to remove residual wash. Let the Spin Column CB2 stand for several minutes, and make it air-dry thoroughly.
7) Place the Spin Column CB2 in a clean 1.5 ml eppendorf tube. To elute DNA, add 30-50 µl Buffer EB to the center of membrane, let the column stand for 2 min, and centrifuge for 2 min at 12,000 rpm (~13,400×g) to collect target DNA.

2. Digestion of Genomic DNA and Gel Electrophoresis (1) Digestion of genomic DNA, digestion solution contained 10 µg of genomic DNA, 5 µl EcoR I and 5 µl Nhe I, and 10 µl 10×H buffer. Add distilled water making the final volume 100 µl. Run the digestion at 37° C. for 12 hours.

(2) Agarose gel electrophoresis, the DNA fragments are electrophoresed with voltage 15V (or 1V/cm) on an 0.7% agarose gel at 37° C. for 20 hours. When the bromophenol blue arrives at 1 cm to the bottom, stopped the electrophoresis.

3. Transfer (1) Cut the gel into sheet with size of 7.5×10 cm, then put it in plate and wash it with distilled water.
(2) Add denaturation solution (1.5 M NaCl, 0.5 M NaOH), and wash gel in it at room temperature for 20 minutes.
(3) Wash the gel with distilled water twice.
(4) Add neutralization solution (1.5 mol/L NaCl, 0.5 mol/L Tris-HCL), wash the gel in it at room temperature for 20 minutes.
(5) Wash the gel with distilled water twice.
(6) Add 20×SSC solution, and balance for 20 minutes.
(7) Set up transfer, with glass plate and weight on top, and let transfer for 14 hours.
(8) Take off blotting material and mark the position of the wells. Soak the membrane in 6×SSC, and put it on filter paper to dry it. Immobilize the DNA by UV-crosslinking (5000 µJ/cm2).
(9) Take out, and photograph the gel with a ruler adjacent to the molecular weight markers as a reference.

4. Hybridization (1) Prehybridization, Place membrane in hybridization bottle with 10 ml of high-effective prehybridization buffer. Incubate in hybridization bottle oven at 65° C. for 3 hours.
(2) Denature probe, prepare probe with concentration of 3 ng/ml, and put it into 1.5 ml eppendorf tube. Denature probe for 10 minutes in boiling water bath, and chill the probe on ice-water immediately for 5 minutes.
(3) Hybridization, discharge the prehybridization buffer, add denatured probe to hybridization solution, and incubate blot at 65° C. overnight.

5. Immunochemiluminescent Detection (1) After hybridization and washing, incubate membrane with wash buffer 1 minute.
(2) Block the membrane with blocking buffer for 30 minutes, and perform this step in shaker rotating at very low speed.
(3) Centrifuge the Anti-Dig-AP for 5 minutes at 13000 rpm. Put 1 µl Anti-Dig-AP into 10 ml blocking buffer, and mix them, preparing Anti-Dig-AP dilution (1:10000).
(4) After blocking, remove the blocking buffer, and add Anti-Dig-AP dilution, soak membrane for 30 minutes at least.
(5) Remove the Anti-Dig-AP dilution, and wash membrane twice in washing buffer, 15 minutes every time.
(6) Remove washing buffer, and equilibrate membrane twice in detection buffer, 2 minutes every time. Incubate with antibody-conjugate for 30 minutes.
(7) Dilute CDP-STAR with detection buffer, and prepare CDP-STAR solution (1:100). Put the membrane into two pieces preservative film, and add CDP-STAR solution. Make the CDP-STAR solution homogeneous diffuse on the surface of membrane, and incubate at room temperature for 5 minutes.
(8) Put the membrane into X-ray film cassette, and expose to film. The time of the exposure is 40 minutes.

Western Blot

The expression of GFP protein was investigated by Western blot, and the results showed that high GFP protein expression driven by the three promoters were detected, as shown in FIG. 5. The manipulation was described as follows:

1. Protein Sample Preparation (1) Total protein extraction from fibroblast
1) Carefully remove culture medium, and clean the culture medium using absorbent paper. Add the 3 ml PBS buffer with 4° C. cold. Place flat and shake gently for 1 minute to wash cells, and remove the washing buffer. Repeat the manipulation twice times, wash the cells three times to remove culture medium. Place flasks on the ice after removing the PBS buffer.
2) Add 100 volumes of lysis buffer to 1 volume of the PMSF, mix the lysis buffer and PMSF, put the mixture on the ice. Add 400 µl mixture to every flask, incubate on ice for 30 min, and shake the flask always full lysis of the cells.
3) After lysating, scrap cells in flasks side with a clean spatula. Collect the mixture of cell fragments and lysis buffer, and transfer to a microcentrifuge tube using pipette. At 4° C., centrifuge samples at 12000 rpm for 5 minutes, and collect supernatant for next manipulation.

(2) Total protein extraction from tissue
1) Break the frozen tissue into small pieces, and transfer them into a 2 ml microcentrifuge tube.
2) Add 400 µl lysis buffer (containing PMSF) to the tube, and homogenize the tissue using homogenizer, then place them on ice.
3) Bread the tissue again in few minutes later, repeat this manipulation some times to make tissue homogenized enough.
4) Lysate the tissue on ice for 30 minutes. After lysis, centrifuge samples with 4° C. at 12000 rpm for 5 minutes, and collect supernatant for next manipulation.

2. SDS-PAGE Electrophoresis (1) Assemble glass plates and spacers in gel casting apparatus.
(2) Compound the 10% resolving gel solution, mix the components after adding TEMED, and pour the resolving gel mixture into the gel plates immediately. When the resolving gel arrives at middle line in green brand, stop pouring. Place a layer of $H_2O$ over the top of the resolving gel to speed up formation of resolving gel.

(3) When there is a refraction line between water and resolving gel, the gel clots. Then stand resolving gel for 3 minutes, and drain the $H_2O$ from top of the resolving gel. Drain any remaining $H_2O$ away with a wipes.

(4) Compound the 4% stacking gel solution, mix the components after adding TEMED, and pour the stacking gel solution into the gel plates immediately. When gel plates are filled, and insert comb to the top of the spacers. When the gel is poured into gel plates, the gel solution is flowing along the plates to avoid creation of bubble. When insert the comb, place the comb flat. After the gel clots, pinch on both sides of the comb straight up and gently pull it out.

(5) Wash the stacking gel, and put it into electrophoresis tank. Pick up samples, add 1×SDS loading buffer. Before loading sample, put the protein into boiling water to denature protein. Then add enough electrophoresis buffer, and load samples.

(6) Electrophoresis, run the gel at 40 V for 4-5 hours, stop the electrophoresis until the dye front just runs out, and transfer the gel to membrane.

3. Transfer (1) Prepare clips for transferring membrane, two sponge pads, a glass rod, wipes and membrane soaking. Open the clip, place the black side flat. Put one sponge pad on the upside, and roll glass rod back and forth several times to remove air bubble. Put three wipes on the pad, fix wipes in one hand, and roll glass rod to remove air bubbles in another hand.

(2) Uncover the glass plates, and scrape the stacking gel gently to avoid destroy the resolving gel. Put the resolving gel on the wipes, adjust resolving gel and wipes aligning. Roll the glass rod gently to remove air bubbles. Cove the gel with membrane entirely, and remove the air bubbles. Put three wipes on it, and remove the bubbles. Then put another sponge pad on it, and close the clip.

(3) Put the clip into transfer tray, transfer at 40V for 3 hours.

(4) After transferring, add 1× ponceau staining solution, strain the membrane for 5 minutes. Wash the membrane to remove destained solution, dry the membrane for next manipulation.

4. Antibody Reaction (1) Soak the membrane with TBS buffer from the bottom up, and transfer it to plates containing blocking solution. Put it into shaker, and shake it for 1 hour.

(2) Dilute the primary antibody with TBST buffer, add the primary antibody solution on the plastic wrap. Take membrane out from blocking solution, and absorb the residual solution. Put the membrane on the plastic wrap with protein facing to antibody, and tilt corners of the membrane to remove air bubbles. Incubate the membrane at room temperature, wash it twice times for 10 minutes with TBST buffer at room temperature on shaker, and wash it TBS buffer for 10 minutes.

(3) Use the same protocol for incubating membrane with secondary antibody at room temperature for 1-2 hours. Wash it twice times for 10 minutes with TBST buffer at room temperature on shaker, and wash it TBS buffer for 10 minutes. Then take chemiluminescence reaction place.

5. Detection (1) Mix same volume of A and B solution on the plastic wrap for one minute. Soak the protein on the membrane with mixture solution for one minute, transfer the membrane to another fresh plastic wrap. Remove the residual solution, package the membrane and put it into X-ray film cassette.

(2) In dark room, add 1× developer solution and fixer solution into plastic tray. Take out X-ray film in red light, and cut it into proper size. Open the X-ray film cassette, and put X-ray film on the membrane. Close the cassette, and expose to film. After exposing, soak the X-ray film into developer solution quickly, when the bands are clear, stop developing.

6. Gel Image Analysis

Scan or photograph the film, identify the molecular weight and photosynthesis density of target bands using gel image processing system.

Q-PCR Analysis of GFP Expression in Transgenic Cells and Transgenic Embryos

Total RNAs were extracted from each sample using the PureLink™ Micro-to-Midi system (Invitrogen) according to the manufacturer's instructions, and reverse transcription was used to generate cDNAs using PrimeScript™ RT Reagent Kit (TaKaRa). Real-time PCR to detect GFP transcripts was performed using SYBR Premix Ex Taq™ (TaKaRa). Amplification reactions were performed in a 20 µl reaction mixture containing 200 ng template cDNA, 0.25 µmol·$L^{-1}$ of each primer, and 10 µl of 2×SYBR Premix Ex Taq buffer. The reaction solution was mixed on MicroAmp™ Optical 96-Well Reaction Plate, and them were sealed MicroAmp™ Optical Adhesive Film (ABI). The PCR was performed on 7500 Real-Time PCR System (Applied Biosystems), with the following parameters: 95° C. for 10 sec, followed by 40 two steps cycles at 95° C. for 5 sec and at 60° C. for 31 sec, then 95° C. for 15 sec, 60° C. for 30 sec, 95° C. for 15 sec, at last it was dissociation stage. The PCR amplification data were collected and analyzed using software Sequence Detection System. The relative expression levels of GFP at different development stages were shown in FIG. 6.

Example 5

Development of in Vitro Transgenic Pig Embryos

TABLE 1

The development of GFP cloned embryos in vitro

| Groups | Embryos | Fusion (%) | Cleavage (%) | Blastocyst (%) | Cell No. of blastocyst | GFP positive blastocyst (%) |
|---|---|---|---|---|---|---|
| PFF | 87 | 71.3 ± 3.2 (n = 62) | 82.4 ± 5.4 (n = 51) | 19.4 ± 6.2 (n = 12) | 36.3 ± 4.7 | — |
| tPFF | 220 | 70.0 ± 2.6 (n = 154) | 85.7 ± 5.0 (n = 132) | 22.1 ± 4.5 (n = 34) | 31.4 ± 3.4 | 77.8 ± 2.2 (n = 27) |

The PFF were wild type fibroblast cells (control group), and the tPFF were transgenic positive cells (experiment group, GFP positive). These two cells were used as nuclear donors for cloning embryos as described below. There was no significant difference between the control group and the experiment group in the fusion rate, the cleavage rate, the blastocyst rate and the cell No. of blastocyst. There were 27 embryos cloned from transgenic positive cells, among transgenic cloned embryos, GFP were identified expression in 21 clone embryos, the GFP positive blastocyst was 77.8%. The results indicated that the porcine ROSA26 could mediate target gene expression highly in embryos cells, and it had no significant affects on development of embryos cells. The fluorescence analysis of transgenic embryos cell was shown in FIG. 7.

The fusion protocol used for somatic cell nuclear transfer (SCNT) is described as follows: aspirate the spindle and first polar body of MII oocytes. Select a transgenic cell as donor, and eject the donor cell into the zonae pellucidae. Place the donor cell well connect to cytoplasma membrane of oocytes, and fusion of nuclear transfer couplets is induced by two 30-μs direct current pulses of 1.2 kV/cm, which makes donor cell and oocytes without nuclear fuse to reconstruct a new embryo and activate it. These tools, buffers and apparatus are listed as follow: fixed pipet (internal diameter is 30 um), injection pipe (internal diameter is 25 um), oocytes ordinary operating medium is improved TCM199 medium, and the oocytes ordinary micromanipulation medium is TCM-199-Hepes plus 7.5 mg/ml cytochalasin B. Fusion medium contains 0.3M mannitol, 1.0 mM $CaCl_2$, 0.1 mM $MgCl_2$, and 0.5 mM HEPES. Micromanipulator system is NT-88NE (Narishige, Japan). Cell fusion equipment is BTX Elector-Cell Manipulator 2001 (BTX, USA). These embryos were cultured in porcine zygote medium-3 (PZM-3) at 38.5° C. in 5% $CO_2$ in air. The cleavage rate (embryos containing two and more than two blastomeres) and the blastocyst rate were assessed at 120 hours after activation, and cell number of embryos with green fluorescence was examined.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A gene targeting vector for site-specific integration and stable expression of a target gene in a transgenic pig, wherein the gene targeting vector comprises a 5' arm and a 3' arm of the sequence of SEQ ID NO:1 and the target gene is inserted between the 5' arm and 3' arm of the sequence of SEQ ID NO:1, wherein the total length of the 5' arm and the 3' arm is the full length of the sequence of SEQ ID No. 1.

2. The gene targeting vector of claim 1, wherein the 5' arm and 3' arm of the sequence of SEQ ID NO:1 is 1.33 kb and 3.6 kb in length, respectively.

3. The gene targeting vector of claim 1, wherein the DNA sequence of the gene targeting vector is SEQ ID NO:2.

* * * * *

SEQUENCE LISTING

```
<160> NUMBER OF SEQ ID NOS: 12

<210> SEQ ID NO 1
<211> LENGTH: 4936
<212> TYPE: DNA
<213> ORGANISM: pig

<400> SEQUENCE: 1
cgggagtgcg gcccgccctg cggcaaccgg aggggagg agaagggagc ggaaaagcct      60
ggaatacgga cggagccatt gctcccgcag agggaggagc gcttcctgct cttctcttgt     120
cactgattgg ccgcttctcc tcccgccgtg tgtgaaaaca caaatggcgt gttttggttg     180
gagtaaagct cctgtcagtt acagcctcgg gagtgcgcag cctcccagga actctcgcat     240 tgcccctgg gtgggtaggt aggtgggtg gagagagctg cacaagaggg cgctgtcggc      300
ctcctgcggg gggagggag ggtcagtgaa agtggctccc gcgcgggcgt cctgccaccc     360
tcccctccgg gggagtcggt ttacccgccg cctgctcggc tttggtatct gattggctgc     420
tgaagtcctg ggaacggccc cttgttattg gcttgggtcc caaatgagcg aaaccactac    480
gcgagtcggc agggaggcgg tctttggtac ggccctcccc gaggccagcg ccgcagtgtc     540
tggcccctcg ccctgcgca acgtggcagg aagcgcgcgc aggaggcggg ggcgggctgc    600
cgggccgagg cttctgggtg gtggtgactg cggctccgcc ctgggcgtcc gccgcctgaa     660
ggacgagact agctctacct gctctcggac ccgtgggggt ggggggtgga ggaagtgagt    720 gggggtcgg tcctgctggc ttgtgggtgg gaggcgcatg ttctccaaaa acccgcgcga    780
gctgcaatcc tgagggagct gcagtggagg aggcggagag aaggcgcacc cttctccgca    840
gggggagggg agtgccgcaa tacctttatg ggagttctct gctgcctcct tttcctaagg    900
accgccctgg gcctagaaaa atccctccct ccccgcgat ctcgtcatcg cctccatgtc      960
agtttgctcc ttctcgatta tgggcgggat tcttttgccc tggcttaacc tgattcttgg   1020
gcgttgtcct gcagggatt gagcaggtgt acgaggacga gcccaattc tctatattcc      1080 cacagtcttg agtttgtgtc acaaaataat tatagtgggg tggagatggg aaatgagtcc  1140
aggcaacacc taagcctgat tttatgcatt gagactgcgt gttattacta aagatctttg    1200
```

-continued

```
tgtcgcaatt tcctgatgaa gggagatagg ttaaaaagca cggatctact gagttttaca    1260
gtcatcccat ttgtagactt ttgctacacc accaaagtat agcatctgag attaaatatt    1320
aatctccaaa ccttaggccc cctcacttgc atccttacgg tcagataact ctcactcata    1380
ctttaagccc attttgtttg ttgtacttgc tcatccagtc ccagacatag cattggcttt    1440
ctcctcacct gttttaggta gccagcaagt catgaaatca gataagttcc accaccaatt    1500
aacactaccc atcttgagca taggcccaac agtgcattta ttcctcattt actgatgttc    1560
gtgaatattt accttgattt tcattttttt cttttcttta agctgggatt ttactcctga    1620
ccctattcac agtcagatga tcttgactac cactgcgatt ggacctgagg ttcagcaata    1680
ctccccttta tgtcttttga atacttttca ataaatctgt ttgtattttc attagttagt    1740
aactgagctc agttgccgta atgctaatag cttccaaact agtgtctctg tctccagtat    1800
ctgataaatc ttaggtgttg ctgggacagt tgtcctaaaa ttaagataaa gcatgaaaat    1860
aactgacaca actccattac tggctcctaa ctacttaaac aatgcattct atcttcacaa    1920
atgtgaaaaa ggagttccct cagtggacta accttatctt ttctcaacac cttttctttt    1980
gcacaatttt ccacacatgc ctacaaaaag tacttttctg ctcaagtcac actgagttga    2040
ttgctattta ccaaaatcaa agtaacatta tcagatctct gtagggtggt ccctctggaa    2100
atgctaccct ccatagtcct tacccttcaa gtaaagagca tgaagactga aatatctcct    2160
ctgtgatctg tcatccttta agccagaatc ccccataaaa aagttagtat tgctttctcc    2220
tgatcccata gcaggttgaa tcatagcact tatcaggttg ttgtcattgc ttgcttaaat    2280
tctcctaact atttggagct tcttgagggc acaggtcttg ttgagtctt gtacctaagc     2340
acctagtata gtccttgatg tctagccaac cctaaataaa atgcagtgag tgacatgtag    2400
atgtctttat aaggtttgat aggttggtct ctcaaatagt tcttttgtat gtttggtagt    2460
gctctagatt agcactggcc agtataactc tgatgatgga aatgttctat agctatgctg    2520
tctaatatgg tagtcactac taacatatgt tactgttgag ccttggaagt atggcttttg    2580
tgacaaaact gaattttttca tgctatgtaa tttaagtcta aattgctact gtgtacattg    2640
tggctgtagc cacaaattg tgctgtggat tgcagaataa ttaatatgga cattgataat     2700
tttcttttca tactaagcag taaggaaaga aaagttgaaa ctctgtggtc catttaggtt    2760
atatgtgtat ttgtacttga ttggtttgtt tgaataccta tttctatact ttagctgaga    2820
gctaaagcca acaaaccagt actgtagata acctgctttg gacaacaatg tgttgactag    2880
ttggatttca ccaaagaatg cctaataaat tttaagaaaa tgagatttca ttaaaccata    2940
atactgacat aagtttaggg aagaatcaga ctatatctgg tgtttgtgaa actacccctg    3000
aatttcagtc ctacaaagtt ttcagttttg gaaaaacttt catcagagag ggcactaagt    3060
tacaggaagc catcacaaag taagttttca tctgatgaat tataaattta agatatattt    3120
taataccaaa attctttatg gtttatgtgc taacttaaaa tttctcctta aaatatgaga    3180
actaagtaca caattgtact tggctgttta atgcggattc ccagtccctc acacagagat    3240
tctcaattaa gattggagag caggggttac tagaattctt tttcaggttc cttatatgct    3300
tctgatttgg tggcctagaa atcacaatgc tagtgcagcc ctcatgggc tacagtatac      3360
gtatctgaaa catgattaca tcagggaaac tgtatgtcta atctactttg tccctaaagg    3420
aagcattttg aaaggcagaa agtaaatatgt gatagttttt gaaacttgta ggtcacattg    3480
tttttaaaag ggatccaagt aagttttttt ttcttttgag ggctacacct gtggcacatg    3540
gaggttccca ggctaggggt taaatcagaa ctgcagctgc cagcctatgc cagagccaca    3600
```

```
gcaatgccag atctgagctg tgtctgcaac tgtgtagctc acagcaacgc tggatcctta    3660
acccaatgag caaggccaga gattgaacct acaacctcgt ggttcctagt tagatttgtt    3720
tccgctgtgc cacgatggga actccaagta atttttttt gagcaaggaa gttaccttt     3780 ttgtctgttt tcccactaaa tgcattcctc aaggattccc agtttgttct tgattcctca    3840
gtgccttaac acagacctgg gttctcagta aatgttgatt ttattgattt atatgtgaaa    3900 ttgttttca aataatagtt tttaagtcca tagaaacaat gcttctttta tggagatact    3960
ttaggatcat acttgtaacc caagttgcct aatactctgt tcataaagaa aactcatgcc    4020
tcatggtctc tgaataatac atctgtctac cattgagctc ttccttgggt ttcctgtgca    4080
aaccattgca cttatcctct tcctgtgcta tacttcctca ggctttatta cagttttaa    4140 aataaaccaa ctatctatct ctctttgaag tagagccata ataattgcat gagaacactg    4200
aaggttttta ggctttaatt ttttctttt ttttaagata ttcaaaattt ggagttcttg    4260
ttgtggcgca gtggttaacg aacccaacta ggaaccatga cgctgcaggt tcggtccctg    4320
gcctcgctca gtgggttaag gatccagcgt tgccatgagc tgtggtatag gtccatatgt    4380
ggctcggatc ctgcattgct gtggctgtgg cagcagccac aggtacgatt agacccctag    4440
cctgggaccc tccatatgct gtgggcgcgg tcctagaaaa gaaaaaaaaa agaaaagaa    4500 aagaaagata tacaaaattt gaactacgca ttgtttctct taacagttgt tatgtatgga    4560
ggaggtttgt tataattaca gtttacaact cttaatccag aatatgttag ggatccacat    4620
tcccagggta agactagttt gttttaggcc agacttaatt gtacagccca ttgtccagcc    4680
acatactcag gagtctcata ctttgcaggc taaaaattct tgattttgtt acctagtagt    4740
gtactgttca tgttggggaa cttttttctc cagaaaagtt tattatccat tatcctgcct    4800 ccttttatt ttcatttatt tatttattta ttttgcttt tttagggcca cacttgtggc    4860
atatggaaat tcctgggcta ggggtcaaat cagggcttca gctgctggcc tatgccacaa    4920
caacacggga tcagag                                                    4936

<210> SEQ ID NO 2
<211> LENGTH: 11997
<212> TYPE: DNA
<213> ORGANISM: Artificial Sequence
<220> FEATURE:
<223> OTHER INFORMATION: Gene Targeting Plasmid Sequence

<400> SEQUENCE: 2
ctcgagttag gcccagcgcg gcgccacggc gtttcctggc cgggaatggc ccgtgcccgt      60 ggggggtgggg ggcaaaaagg cggagcgagc caaaggcggt gaggggggag ggccagggaa    120
ggaggggggg gccggcacta ctgtgttggc ggactggcgg gactggggct gcgtgagtct    180
ctgagcgcag gcgggcggcg gccgcccctc ccccggcggc ggcggcggcg gcggcggcgg    240
cggcagcagc tcactcagcc cgctgcccga gcggaaacgc cactgaccgc acggggattc    300
ccagcgccgg cgccaggggc acccgggaca cgccccctcc cgccgcgcca ttggcccctc    360
cgcccaccgt ctcgcaccca ttggccagct cccgccaat cagcggaagc cgccggggcc    420
gcctagagaa gaggctgtgc tctggggctc cggctcctca gagagcctcg gctaggtagg    480
ggagcgggac tctggtttgg gggaggggccg gcggtttggc gggggatggg tgcttgaggt    540
ggtctgaccg gtagcggggg tcgccttccc tagcgggaag tcgggagcat atcgtttgtt    600
acgctggaag gggaagaggt ggtgagaggc aggcgggagt gcggcccgcc ctgcggcaac    660
```

```
cggaggggga gggagaaggg agcggaaaag cctggaatac ggacggagcc attgctcccg    720
cagagggagg agcgcttcct gctcttctct tgtcactgat tggccgcttc tcctcccgcc    780
gtgtgtgaaa acacaaatgg cgtgttttgg ttggagtaaa gctcctgtca gttacagcct    840
cgggagtgcg cagcctccca ggaactctcg cattgccccc tgggtgggta ggtaggtggg    900
gtggagagag ctgcacaaga gggcgctgtc ggcctcctgc ggggggaggg gagggtcagt    960
gaaagtggct cccgcgcggg cgtcctgcca ccctcccctc cggggagtc ggtttacccg    1020 ccgcctgctc ggctttggta tctgattggc tgctgaagtc ctgggaacgg cccttgtta    1080 ttggcttggg tcccaaatga gcgaaaccac tacgcgagtc ggcagggagg cggtctttgg    1140
tacggccctc cccgaggcca cgccgcagt gtctggcccc tcgcccctgc gcaacgtggc    1200
aggaagcgcg cgcaggaggc ggggcggcc tgccggcccg aggcttctgg gtggtggtga    1260
ctgcggctcc gccctgggcg tccgccgcct gaaggacgag actagctcta cctgctctcg    1320
gacccgtggg ggtgggggt ggaggaagtg agtgggggt cggtcctgct ggcttgtggg    1380
tgggaggcgc atgttctcca aaacccgcg cgagctgcaa tcctgaggga gctgcagtgg    1440
aggaggcgga gagaaggcgc acccttctcc gcaggggag gggagtgccg caatacccttt    1500 atgggagttc tctgctgcct ccttttccta aggaccgccc tgggcctaga aaaatccctc    1560
cctcccccgc gatctcgtca tcgcctccat gtcagtttgc tccttctcga ttatgggcgg    1620
gattcttttg ccctggctta acctgattct tgggcgttgt cctgcagggg attgagcagg    1680
tgtacgagga cgagcccaat ttctctatat cccacagtc ttgagtttgt gtcacaaaat    1740
aattatagtg gggtggagat gggaaatgag tccaggcaac acctaagcct gattttatgc    1800
attgagactg cgtgttatta ctaaagatct ttgtgtcgca atttcctgat gaagggagat    1860
aggttaaaaa gcacggatct actgagtttt acagtcatcc catttgtaga cttttgctac    1920
accaccaaag tatagcatct gagattaaat attaatctcc aaaccttagg cccctcact    1980 tgcatcctta cggtcagata actctcactc atactttaag cccatttgt ttgttgtact    2040 tgctcatcca gtcccagaca tagcattggc tttctcctca cctgttttag gtagccagca    2100
agtcatgaaa tcagataagt tccaccacca attaacacta cccatcttga gcataggccc    2160
aacagtgcat ttattcctca tttactgatg ttcgtgaata tttaccttga ttttcatttt    2220 tttcttttc ttaagctggg attttactcc tgaccctatt cacagtcaga tgatcttgac    2280
taccactgcg attggacctg aggttcagca atactcccct ttatgtcttt tgaatacttt    2340
tcaataaatc tgtttgtatt ttcattagtt agtaactgag ctcagttgcc gtaatgctaa    2400
tagcttccaa actagtgtct ctgtctccag tatctgataa atcttaggtg ttgctgggac    2460
agttgtccta aaattaagat aaagcatgaa ataactgac acaactccat tactggctcc    2520
taactactta aacaatgcat tctatcttca caaatgtgaa aaaggagttc cctcagtgga    2580
ctaaccttat cttttctcaa caccttttc tttgcacaat tttccacaca tgcctacaaa    2640
aagtactttt ctgctcaagt cacactgagt tgattgctat ttaccaaaat caaagtaaca    2700
ttatcagatc tctgtagggt ggttccctct ggaatgctac cctccatagt ccttacccttt    2760 caagtaaaga gcatgaagac tgaaatatct cctctgtgat ctgtcatcct ttaagccaga    2820 atccccata aaaaagttag tattgctttc tcctgatccc atagcaggtt gaatcatagc    2880
acttatcagg ttgttgtcat tgcttgctta aattctccta actatttgga gcttcttgag    2940
ggcacaggtt cttgttgagt cttgtaccta agcacctagt atagtccttg atgtctagcc    3000
aaccctaaat aaaatgcagt gagtgacatg tagatgtctt tataaggttt gataggttgg    3060
```

```
tctctcaaat agttctttg tatgtttggt agtgctctag attagcactg gccagtataa   3120
ctctgatgat ggaaatgttc tatagctatg ctgtctaata tggtagtcac tactaacata   3180
tgttactgtt gagccttgga agtatggctt ttgtgacaaa actgaatttt tcatgctatg   3240
taatttaagt ctaaattgct actgtgtaca ttgtggctgt agccacaaat ttgtgctgtg   3300
gattgcagaa taattaatat ggacattgat aatttctttt tcatactaag cagtaaggaa   3360
agaaaagttg aaactctgtg gtccatttag gttatatgtg tatttgtact tgattggttt   3420
gtttgaatac ctatttctat actttagctg agagctaaag ccaacaaacc agtactgtag   3480
ataacctgct ttggacaaca atgtgttgac tagttggatt tcaccaaaga atgcctaata   3540
aattttaaga aaatgagatt tcattaaacc ataatactga cataagttta gggaagaatc   3600
agactatatc tggtgtttgt gaaactaccc ctgaatttca gtcctacaaa gttttcagtt   3660
ttggaaaaac tttcatcaga gagggcacta agttacagga agccatcaca aagtaagttt   3720
tcatctgatg aattataaat ttaagatata ttttaatacc aaaattcttt atggtttatg   3780
tgctaactta aaattctcc ttaaaatatg agaactaagt acacaattgt acttggctgt   3840
ttaatgcgga ttcccagtcc ctcacacaga gattctcaat taagattgga gagcaggggt   3900
tactagaatt cttttcagg ttccttatat gcttctgatt tggtggccta gaaatcacaa   3960
tgctagtgca gccctcatgg ggctacagta tacgtatctg aaacatgatt acatcaggga   4020
aactgtatgt ctaatctact ttgtccctaa aggaagcatt ttgaaaggca gaaagtaata   4080
tgtgatagtt tttgaaactt gtaggtcaca ttgtttttaa aagggatcca agtaagtttt   4140 ttttctttt gagggctaca cctgtggcac atggaggttc ccaggctagg ggttaaatca   4200
gaactgcagc tgccagccta tgccagagcc acagcaatgc cagatctgag ctgtgtctgc   4260
aactgtgtag ctcacagcaa cgctggatcc ttaacccaat gagcaaggcc agagattgaa   4320
cctacaacct cgtggttcct agttagattt gtttccgctg tgccacgatg ggaactccaa   4380 gtaattttt tttgagcaag gaagttacct tttttgtctg ttttcccact aaatgcattc   4440
ctcaaggatt cccagtttgt tcttgattcc tcagtgcctt aacacagacc tgggttctca   4500
gtaaatgttg atttattga tttatatgtg aaattgtttt tcaaataata gttttttaagt   4560 ccatagaaac aatgcttctt ttatggagat acttaggat catacttgta acccaagttg   4620
cctaatactc tgttcataaa gaaaactcat gcctcatggt ctctgaataa tacatctgtc   4680
taccattgag ctcttccttg ggtttcctgt gcaaaccatt gcacttatcc tcttcctgtg   4740
ctatacttcc tcaggcttta ttacagtttt taaaataaac caactatcta tctctctttg   4800
aagtagagcc ataataattg catgagaaca ctgaaggttt ttaggcttta attttttctt   4860 ttttttaag atattcaaaa tttggagttc ttgttgtggc gcagtggtta acgaacccaa   4920
ctaggaacca tgacgctgca ggttcggtcc ctggcctcgc tcagtgggtt aaggatccag   4980
cgttgccatg agctgtggta taggtccata tgtggctcgg atcctgcatt gctgtggctg   5040
tggcagcagc cacaggtacg attagacccc tagcctggga ccctccatat gctgtgggcg   5100
cggtcctaga aagaaaaaa aaaagaaaa gaaaagaaag atatacaaaa tttgaactac   5160
gcattgtttc tcttaacagt tgttatgtat ggaggaggtt tgttataatt acagtttaca   5220
actcttaatc cagaatatgt tagggatcca cattcccagg gtaagactag tttgtttag   5280 gccagactta attgtacagc ccattgtcca gccacatact caggagtctc atactttgca   5340
ggctaaaaat tcttgatttt gttacctagt agtgtactgt tcatgttggg gaactttttt   5400
```

```
ctccagaaaa gtttattatc cattatcctg cctcctttt  attttcattt atttatttat   5460
ttatttttgc ttttttaggg ccacacttgt ggcatatgga aattcctggg ctaggggtca   5520
aatcagggct tcagctgctg gcctatgcca caacaacacg ggatcagagc tgcatctgca   5580
atctatacca cagcttttgg caaccccgta tccttaaccc aatgaatact agttgggttc   5640
ttaacccgct aagccataat tggaactccc atgatcccca ttcttgatga agtgggtgag   5700
aaactggttt attaaagaac tattaatagc atggaatgaa atatttaggt ctgttttatc   5760
taggccagag tcaaacttga tgacttatta ctggtgtcat ggtgtatacc tttcttgctg   5820
actagagact atttctgcct ctctgattgt atctcaaagt catggttgca tttaatccta   5880
cttttccagc cttttccccc agatatttag tttgtactgg tacttagtca ccctttgttt   5940
tctaggtttg tttgttttt  ttttttttaa acatgtttgt gattggcttt tcctgctgac   6000
aacagtaaca cattttctca gcacatttat agaattcgtt attttactag ctaactaacc   6060
ccaccctcta gtgtagggac agtggttttt tcttttttatt aacctttggt taaaatccca   6120
ccccagactt tttattacaa gtaatagcaa tttaccctag tgcataccat aggcaaaagc   6180
taatggaaat gtaggttaga agaaatgaac taatattcgt tgagtgacag ttctgtacca   6240
gttagtatgg cagacttgcc agtgagttta gtgtggttct gatgtataaa acttcatctt   6300
acagagtgtg aaactaaagc tcagtgaggt ttaataattc tcctgtaaac acagcaatta   6360
ggagctacag attcaaaatt ctaatctgac ttacctagtc ggtatccctt acttagctta   6420
gggtaccatg tttctctata gaaacagtct tttaggaaat ttaatctggc tacagataca   6480 ggatggggttg taggggttgaa ggcagagaga ccaaacttag gagattcttt tacagtagtc   6540
ctgacaggaa gcgatggggt ctgttataca atgatggcaa tcaaaatgga aaggaagtta   6600
aaggactctg aacaccagtc actgaaaaga atggtctcaa cacatcactt ttcaaggaag   6660
ccttccttga tgcccttaac tccacgatat tggattcccc acttgaaagc tgtcatagca   6720
cttctcacaa ctgtattaga ttagtaagtg ggggaattt  ttttttgctt tttaaggttg   6780
ctccttgagg ggatgatggt gcttatattc ctgttgtcta atcatagggga ggtcttcagg   6840 tcaaaactat tttcatagga attctctggt ggcctatggg ttaaggattt ggcattgtca   6900
ctgctgtggg tgtggccaga gcccattttt ttttttctcaca ggtgtgtagg ggctatgtga   6960
attttccaga atttcccaag gttgtaggtt tatgttttgt aacttttagaa attaactttc   7020 tttaggttat acctctaaaa tcccaccaac cttcagaatt atgtaattgc tactacaaaa   7080
ctctgtagtt aaatacattc tgtggtcttg ttatgaaata aagttttaaa tattttctca   7140
caacttatta acttttaaat ttaattacaa cttgttttag aattttgggg ggggggcttt   7200
cctcaaggta tatggtgttc tgggccaggg atcagatgtg agccactgtt tgacctacac   7260
tgcagctatg gcaacgctgg atcctttaat cccttgtgtg gtgccaggga ctgaacctgc   7320
gttctggcac tgcagagaga gatgctgctg atcttactca gccacagcag gaaccccctag   7380 gatttaataa tttattcaaa ataaaccaat ttttcttatt atataaatac tatatataga   7440
tactataagt aatatttttt aagaatagat cattggctta aaaaatgaca tgttcagccc   7500
acaactacac catctatgtt taaaaatgct aagaagatga agttaataga aactataagg   7560
aaaacctact gaagtatctt aaatgataaa ttatataaca tatggctggc agatcataca   7620
tattagtgga gaaactttac aaaaagccat aaacagctga tgctcttgaa tgatgaaaag   7680
taaaaattca tggtagtgct gctttataac aatatagtaa cttgttaaga tttatgctca   7740
gacatgaagt ctgttaatac cacattggta gcactgtatg tgtgcctcac aatagatgag   7800
```

```
ttttcaaaca tggttgggct tgttatgttg cttttacctg tctggcatta gcagctagtc    7860
agactcttaa catgaagtgc gacaaacaca acatgtccta ttaaataact ttaaaatctt    7920
aacggtttat cctgaccttt tcactaatgg tgaaacgcaa acgtgggtaa aactgccagg    7980
acttggcaga aagaaagaca gtggcacaaa actagcagtc attttctgcc atccatttgc    8040 agaataggggg gtggcagttt cacttaaaga atgtccttgt gtgggagttc ccgtcgtggt    8100
tcagtggtta atgaatccga ctaggtaccg tgaggttgca ggtttgatcc ctggccttgc    8160
tcagtgggtt aaggatcccg agttgctgtg gctctggcgt aggccggtgg ctacggctcc    8220
aattcagccc ctagcctggg aacctccata ttgctgaggg agtggcccaa gaaatggcaa    8280
aaggaaaaaa aaaagtcct tgtgaaaaca aattatttga ttaaatctgg accgtgagta     8340
cataatacac atatgggtga tgaaatggaa agtttgtggt acttcatatg ctaaaaagta    8400
taatggttgt ctcaggaaaa aacattcaag acagttgagt tgcaagctga tttagctcct    8460
attttcttgg aatactaatt ttacttgaaa gattgactgt caaattttga ttgtcacagt    8520
tggatatttg gcagacattt tttcaaatac gaaggaagtt agccttttcaa ggaaaactga   8580 cagcagttgt tgtcaatgat aaaattcaaa cttggaagtg aaaatacaga attctgggga    8640
aacatctatt agcaagaggc tgactatcag tactgtccct agtgttttt tttttttaaa     8700 taagtgagaa tgttagtata acattagata atgcataacg atgtgggcca aaatttggaa    8760 gtttttttt ttttttttt tgtctcttta gggccacacc tgtggcaata tggaggttcc      8820
cacagtaggg atctaattgg agctataact gccagctaga gccacagcaa cgccagatcc    8880
gagccacggc tgtgacctat accacagctc acggcaacac tggatcctta acccagtgag    8940
cgaggccagg gatcctggga acctccatat gccgcgggaa gcggccctag aaaagacaaa    9000
aaaaaaaaaa aaaaaaatcc agctgttttg tacttaggca ttatattaag gcggactgaa    9060
ttgcagaaat ataaaacgtc actcttattt gaaaaataca gttacttccg tgaaaatgtt    9120 aatgtgatttt atttgtcact atgttttttt cccctcagtt ttaatttcta gtatggtaaa   9180
atactggtaa acaaagcatt tgggaccctc agcttttaat aatgtgaaga tatcctgaga    9240
ccaagaagtt ggaggaagct gctaagcata gtgagtatac atggtaaaca ctcaaatgcc    9300
tgttgaatag ctggatgtag tgaaaaatga ctccaggtat taagcctgga ttactgggag    9360
ggtgggcatg ccaggacagg gagcagattt taatggagaa agataggttc aagttgagtt    9420
ttaagtagga caggcagggg taatcacagg aggcagctgg aaattcagaa tttgggcttg    9480
agaaaactaa aataccatgt tttcctttcc agtgaaaatt gctttcatca tagactatat    9540
gattgaatag ctacaatccc acagctgatt agcatacatg tttgccttgg ggcagaagta    9600
tgagggtgac aaagcaggct tctcataagc aatggtaaat ttttcacat tgtgcacatt     9660 aaaaaatgca gtataggaga gagctgtcta tatggtgttc ctcttcaact taaaaataaa    9720
taaataacca aggtacagta tttcaatttt ttttgtgtgt cctagaattt tcaaactttc    9780
atcatattcc cacataatac ctcatctgaa cttcatggaa agggctactt tttctatgcc    9840
tagctcagta gtattaaggc cttttgggct ttattgtaat ttatgtactt tacagattta    9900
aacccctgcc cccggctgcg cccatggcat gtggaaattc ctgagctggg gattagaacc    9960
tatgccacaa ttgtagcctg caccacagct gtggcaaggc cacatcctta acctgctatg   10020
ccaagggagc ttccaatata aaactttaa accacctcct tttttcagt cttagtctta    10080 tcctttggca cttgcaatgg agacctgagt gcatctggca ttgatacaga acctctaaag   10140
```

```
ttttctgaaa gtcttgttac aatgtttaaa aatgtttccc tctctaggca ctagtacact    10200
gacagtcact ggaagataaa tgactttcct ttcattaaaa ttatatttgt ctcagtgtct    10260
tttttccccc cctctaaaat atattgaatg tctggtccat aactcagtca ttttgtgtcc    10320
agattatttt atttatttta atggccacac ccctggcata tggaagttcc tgggccaggg    10380
actgaatccc agctgcagct gcagcaatgc tggatccttt taacccacta cacagggctg    10440
gtgattgaac ccatgccttt gcagcaacct gagctgctgt ggatggattc taacccactg    10500
tgccatggca ggaattgtgt gttcagatta ttaaaattat cttaaccatc ttttataat    10560 cccatgatgc aggaagccca cttcagaagt taaccaaggt cacacaactg gtaggtacct    10620
ggcagtatcg tatagaatct cagttttct gaatcctcat ataatgcatt ttctgtcaac    10680
agataacaaa atattggggt ggggggagat ggcaaatttt tgcagacatt gttcactaca    10740
tacttaattt gaaatcaatc tgttcatgtt tttgggcctt tagctatgat ggaccaagca    10800 taaaaacag ccattatgca aaaatatcca tttgttcaac caatattaaa tactcatgat    10860
aggttttttt ttctttttc ttttttttt tttttttt tttttttt ttttgtcttt    10920 ttgccatttc ttgggccgct cctgcggcat atgaaggttc ccaggctagg ggttgaatca    10980
gagctgtagc catcggccta cgccagaacc acagcaactc gggatccgag ccgtgtctgc    11040
aacctacacc acagctcagg gcaatgccag atccttaacc cactgagcaa gatcagggat    11100
tgaacccgca acctcattgt tcctcgtcgg atttgctaac ctctgagccg tgacaggaac    11160
tccgctggta ggtactttt atcaggtaaa cagtggagaa aacagataag gtccttgaac    11220
ttttccagtt ctgtgttctg gtgaccagag gtttatatat atagtttctt ttgtaaacag    11280
ctttaatgtt gaaccccata atcaactgtg cattctgatg atggtaaaaa ctccagtctg    11340
ggatataaga gccttataag tccttctttc cagttcattc tcatacctct gggaggtagt    11400
atatcagaga ggaaccagac taggactgtt ggctgtgctg ctaatgtgaa ttctgttctt    11460 tcaagggaa gaagtcctat gtcctttct aaatgagacg tccaaagtta acatgaatag    11520
gagttttggc tgtggcgcag tgggttaatg atttggcttg tctctggcag tgccagttct    11580
acccctggcc cagaaacatc catatgccac ggtgcagcca aaaaggggga gaaaacaagt    11640
tgatatgagt agcactatta tgttattaac atgacactga acatctaagc tgaatgcagc    11700
caaaaacaat actactatac agaattccac acaagatccc aacttctctt aatcccaggg    11760
aggtgtttag gttatttcaa ttcctactgt tagcaaagac tttctgcaac aggaaaagca    11820
actaaggatg aatagtgacc aagagtaaac aagaatttac atgaagtttt taattcaaag    11880
acatcagttc tctagtaaag aagcccaaac atcaccacct ttctgtactg aatgaaaaat    11940
aaaatttctt taaatatggc ttgttggtcg catacttcat ctacaaggct ctttgct    11997
```

<210> SEQ ID NO 3
<211> LENGTH: 28
<212> TYPE: DNA
<213> ORGANISM: Artificial Sequence
<220> FEATURE:
<223> OTHER INFORMATION: PCR Primer

<400> SEQUENCE: 3
ggatctaatt ggagctataa ctgccagc                                        28

<210> SEQ ID NO 4
<211> LENGTH: 22
<212> TYPE: DNA
<213> ORGANISM: Artificial Sequence

```
<220> FEATURE:
<223> OTHER INFORMATION: PCR Primer

<400> SEQUENCE: 4
gctgagggtc ccaaatgctt tg                                              22

<210> SEQ ID NO 5
<211> LENGTH: 24
<212> TYPE: DNA
<213> ORGANISM: Artificial Sequence
<220> FEATURE:
<223> OTHER INFORMATION: PCR Primer

<400> SEQUENCE: 5
cgggagtgcg gcccgccctg cggc                                            24

<210> SEQ ID NO 6
<211> LENGTH: 26
<212> TYPE: DNA
<213> ORGANISM: Artificial Sequence
<220> FEATURE:
<223> OTHER INFORMATION: PCR Primer

<400> SEQUENCE: 6
agtagatccg tgcttttaa cctatc                                           26

<210> SEQ ID NO 7
<211> LENGTH: 34
<212> TYPE: DNA
<213> ORGANISM: Artificial Sequence
<220> FEATURE:
<223> OTHER INFORMATION: PCR Primer

<400> SEQUENCE: 7
gagttttaca gtcatcccat tgtagactt ttgc                                  34

<210> SEQ ID NO 8
<211> LENGTH: 29
<212> TYPE: DNA
<213> ORGANISM: Artificial Sequence
<220> FEATURE:
<223> OTHER INFORMATION: PCR Pimer

<400> SEQUENCE: 8
agctctgatc ccgtgttgtt gtggcatag                                       29

<210> SEQ ID NO 9
<211> LENGTH: 23
<212> TYPE: DNA
<213> ORGANISM: Artificial Sequence
<220> FEATURE:
<223> OTHER INFORMATION: PCR Primer

<400> SEQUENCE: 9
gagcaagggc gaggagctgt tca                                             23

<210> SEQ ID NO 10
<211> LENGTH: 21
<212> TYPE: DNA
<213> ORGANISM: Artificial Sequence
<220> FEATURE:
<223> OTHER INFORMATION: PCR Primer

<400> SEQUENCE: 10
tgcagaattc gaagcttgag c                                               21
```

```
<210> SEQ ID NO 11
<211> LENGTH: 24
<212> TYPE: DNA
<213> ORGANISM: Artificial Sequence
<220> FEATURE:
<223> OTHER INFORMATION: PCR Primer

<400> SEQUENCE: 11
gttagtaact gagctcagtt gccg                                          24

<210> SEQ ID NO 12
<211> LENGTH: 23
<212> TYPE: DNA
<213> ORGANISM: Artificial Sequence
<220> FEATURE:
<223> OTHER INFORMATION: PCR Primer

<400> SEQUENCE: 12
gggaaccacc ctacagagat ctg                                           23
```